United States Patent [19]

Allen et al.

[11] 4,066,584

[45] Jan. 3, 1978

[54] ALLOY FIBERS OF RAYON AND COPOLYMERS OF ACRYLIC AND METHACRYLIC ACIDS

[75] Inventors: Thomas C. Allen; David B. Denning, both of Asheville, N.C.

[73] Assignee: Akzona Incorporated, Asheville, N.C.

[21] Appl. No.: 603,483

[22] Filed: Aug. 11, 1975

[51] Int. Cl.$^2$ .................. A61F 13/20; C08L 1/02
[52] U.S. Cl. ..................... 260/17.4 CL; 128/284; 128/285; 260/17 R; 260/17.4 R; 264/191
[58] Field of Search ............. 260/17.4 CL; 128/285, 128/284

[56] References Cited

U.S. PATENT DOCUMENTS

| 3,256,372 | 6/1966 | Adams et al. ............. 260/17.4 |
|---|---|---|
| 3,816,357 | 6/1974 | Church ..................... 260/17.4 |

*Primary Examiner*—Edward M. Woodberry
*Attorney, Agent, or Firm*—Francis W. Young; Jack H. Hall

[57] ABSTRACT

Highly absorbent, cardable cellulosic fibers are made by incorporating therein, an alkali metal or ammonium salt of a copolymer of acrylic acid and methacrylic acid, where the ratio of acrylic acid units to methacrylic acid units (by weight) is from 90:10 to 10:90.

9 Claims, No Drawings

ALLOY FIBERS OF RAYON AND COPOLYMERS OF ACRYLIC AND METHACRYLIC ACIDS

BACKGROUND OF THE INVENTION

This application relates to highly absorbent fibers, for example, viscose rayon, hydroxypropylcellulose, and hydroxyethylcellulose, made from wood pulp or other cellulosic materials, which are useful in the production of nonwoven articles such as diapers, tampons, sanitary napkins, medical sponges, soil mulches, wiping cloths, and the like. Each of these applications requires a material having a high capacity for absorbing and retaining water and other aqueous fluids, particularly, body fluids. Cellulosic fibers have found wide use in these and similar applications because of the hydrophilic nature of the cellulose molecule and its fibrous structure which contributes integrity, form, shape, wicking ability, and liquid retention to a nonwoven material.

Some examples of attempts to increase the absorbency of rayon fibers can be found in U.S. application Ser. No. 330,378, filed Feb. 7, 1973, and U.S. Pat. No. 3,844,287 where alkali metal and ammonium salts of polyacrylic acid are incorporated in regenerated cellulose to increase the fluid absorbency of rayon fibers produced therefrom. Other examples of hydrophilic polymers incorporated into viscose to increase the hydrophilic properties of the fiber are the addition of carboxymethylcellulose and carboxyethyl starch as described in U.S. Pat. Nos. 3,423,167 and 3,847,636, respectively.

It has been previously known that the water absorption of a material depended upon the degree of hydrophilicity it exhibited. Such determinations of water absorption as swelling and water retention under centrifugation can be considered to be dependent on the degree of ionization of the material. Hence, the more strongly acidic that a material incorporated in a fiber is, the more absorptive it will be. In the case of polyacrylic acid, since it is more acidic, i.e., more highly ionized, than polymethacrylic acid, it would be expected that rayon fibers containing injected polyacrylic acid would have a higher water retention value than fibers containing injected polymethacrylic acid. This has been demonstrated, as will be shown later.

One problem that has been found with the approach of incorporating the anionic hydrophilic polymers into cellulosic fibers is the adverse effect on carding properties. An important property which fibers must have to be used in the applications previously mentioned, and especially in the preparation of tampons, is the capability of being carded on conventional carding equipment. The incorporation of polyacrylic acid into viscose rayon fibers by the injection method was found to decrease the sliver cohesiveness significantly. The cohesiveness property is very important in the commercial processing of rayon fibers into useful products such as tampons. If the cohesiveness is too low, then the fibrous material will not cohere, necessitating a reduction in processing speed or other process modifications, or even making the fiber impossible to process. Therefore, it is a primary object of this invention to provide a rayon fiber having improved fluid absorption without an excessive loss in fiber cohesiveness and consequent difficulty in carding the fibers for processing into useful articles.

SUMMARY OF THE INVENTION

It has now been discovered that alkali metal or ammonium salts of certain copolymers will further increase the absorbency and retention properties of rayon when injected into the viscose, and a fiber having a cohesiveness greater than the prior art materials referred to above can be produced. The cohesiveness is extremely important from the standpoint of handling staple fibers in carding equipment prior to the manufacture of finished articles of commerce from the fiber. It is now known why the copolymers of the invention exhibit increased cohesiveness over polyacrylic acid. One factor generally believed to be important in fiber cohesion is the amount of crimp in the fiber. However, both the copolymers of this invention and polyacrylic acid give decreased crimp as the amount of material incorporated into the fiber is increased. Another factor believed to be important in fiber cohesion is the surface bonding properties of the fiber. This surface bonding, which is present in ordinary cellulose, is thought to be due to hydrogen bonding and possibly the stiffness of the fiber. Surface bonding is thought to be the predominating effect exhibited in the invention, possibly due to the higher glass transition temperature (Tg) of the copolymer imparted by methacrylic acid.

Applicants have found that alkali metal and ammonium salts of copolymers of acrylic and methacrylic acid incorporated into the viscose solution improves the absorbency and fluid retention properties of the resulting fiber and, most unexpectedly, cause the fiber spun from the viscose to retain its cohesiveness to such an extent that the fibers can be easily processed on carding equipment, whereas the previously mentioned fibers incorporating equal amounts of the sodium salt of polyacrylic acid, did not card satisfactorily on conventional carding equipment.

DETAILED DESCRIPTION OF THE INVENTION

The fibers of the invention can be prepared by adding, at any stage of viscose aging, but preferably by injecting into the fully ripened viscose solution, an amount of copolymer in the range of 2 to about 40% by weight of cellulose in the viscose solution (hereafter all percentages are given on this basis and referred to as CIV). We prefer the range of 10–20% CIV, based on a balance between increasing absorbency, economic factors, and processing conditions. The viscose solution containing the copolymer is then spun or extruded through spinneret openings into an acid bath where the cellulose fiber is regenerated. The regenerated fiber is stretched in air from 0–100%, or even higher, if desired, preferably from about 30 to 50% and then run through a hot aqueous bath which can be maintained at a temperature of from ambient to 100° C., preferably from 90°–97° C. The hot aqueous bath contains various amounts of dilute sulfuric acid, $ZnSO_4$ and sodium sulfate. The fiber is subjected to a second stretching of from 0 to 100% in the hot bath. The total stretch in both steps is preferably in the range of 50–70%. The stretching, as is well known, imparts the necessary strength to the finished fiber. The fibers, now a large bundle of continuous filaments or tow, from the combined output of a number of spinnerets is cut into short fibers of any desired length and washed and dried to a moisture content of around 11% and baled.

After the fiber is regenerated in the acid bath, the copolymer occluded in the fiber will be in acid form. The copolymer must be in the form of the alkali metal or ammonium salt in order to achieve the highest degree of absorbency. The copolymer of acrylic acid and methacrylic acid is converted to the salt form during an alkaline sodium sulfide wash bath which is conventionally used to remove metal and sulfur impurities. In some instances, it may be desirable, particularly, if an acid wash follows the sulfide, to treat the fiber with a base such as a dilute solution of sodium bicarbonate, sodium hydroxide, and the like, to complete the conversion, and insure that a high percentage of the copolymer is in the salt form. It may be necessary to limit the amount of conversion to the salt form for certain applications where the material may come into contact with the body, since a pH which is much higher than 7 to 7.5 can cause irritation of delicate membranes and serves to promote the growth of harmful microorganisms. Finally, a conventional finish, such as a surfactant, may be applied and the staple fiber is dried in a continuous drier to a predetermined moisture content suited to the particular end use of the fiber.

The fiber can then be baled or carded for processing into one of the final products mentioned previously. A particularly suitable use for the fiber of the invention is for tampons, which may be made, for example, by one of the methods referred to in U.S. Pat. No. 3,699,965, or by other well-known methods.

The copolymers of the invention may be prepared by known methods. In the simplest terms, an amount each of monomeric acrylic acid and methacrylic acid, calculated to give the desired average ratio in the copolymer are mixed together with a polymerization initiator in a reaction vessel and allowed to react until polymerization is completed. Special techniques well-known to those skilled in the art, such as the use of chain transfer agents and other molecular weight regulators, cross-linking agents, surfactants, redox system, controlled monomer addition, and the like, can also be applied to make specialized polymers. A copolymer containing 50% each of units derived from acrylic acid and methacrylic acid is preferred, but ratios from 90:10 (acrylic acid/methacrylic acids) to 10:90 are useful.

The viscosity of the copolymer is an indication of the degree of polymerization (D.P.) and the molecular weight of the copolymer. A wide range of D.P. values has been found to work and the major limitation on D.P. is the processing conditions. For example, a copolymer having a higher molecular weight will generally be retained to a greater degree in the fiber, but if the copolymer is to be injected into the viscose, the molecular weight is limited by the viscosity which can be pumped. However, pumping systems are generally available which can handle fluids at viscosities of 10,000 cps and over. Copolymers of a wide range of viscosities can be used if the copolymer is added to the dissolver.

The absorbency of the fibers can be determined by various test methods. A common measure of absorbency is the Water Retention Value or Secondary Swelling ("Q") which is determined in the manner disclosed in Ser. No. 330,378 referred to above and is hereby incorporated by reference. Briefly, the test measures the amount of water retained by the fiber after centrifuging for 15 minutes at 2500–3000 times gravity from which the percentage of water retained in the sample is calculated (based on dry weight by the fiber sample). A more recent test which correlates well with actual end use evaluations has been developed. The so-called Demand Wettability Test (Lichstein, Bernard, International Nonwovens and Disposables Association, 2nd Annual Symposium on Non-Woven Product Development, Mar. 5-6, 1974, Washington, D. C.), uses a novel apparatus which allows the measure of volume and rate of absorption of a fluid by maintaining the absorbent material at a zero hydrostatic head so that wetting occurs purely on demand by the absorbent material. Thus, the absorption of liquid occurs only by virtue of the ability of the absorbent material to imbibe liquid with the flow of liquid abruptly stopping at the point of saturation. Variations in the method can be made to allow for end product simulation, e.g., the fibrous mass can be compressed to simulate a tampon. Testing of the compressed fiber can then be conducted on the apparatus using a variety of external pressures and testing fluids.

To satisfactorily process fibers into useful products such as tampons or other nonwoven products, it is necessary to align the fibers predominantly in one direction, prior to making the product, often accomplished by carding the fibers. The ability to card the fiber is dependent on the cohesiveness of the fibers, that is, the ability of individual fibers to "cohere together" and permit the sliver or web to be handled without breaking the cohesive mass apart. The cohesion test performed by applicant on the carded fiber is to simply measure the force in grams required to break or separate a carded sliver. The sliver cohesion factor is expressed in terms of grams of force required per grain of fiber.

EXAMPLES

To illustrate the invention, the following examples were prepared.

EXAMPLE 1

A solution of a 90/10 copolymer of acrylic acid and methacrylic acid was prepared and injected into a viscose solution at a concentration of 5% CIV, thoroughly mixed with the viscose and spun into a conventional acid spinbath containing 8.5% sulfuric acid, 5.0% of $MgSO_4$, 3.0% of $ZnSO_4$, 18.2% of $Na_2SO_4$ and 30-35 ppm laurylpyridinium chloride (LPC) at 49°-51° C. to coagulate and regenerate the cellulose to give an 1100 denier yarn containing 480 filaments. The resulting yarn was then run through a fresh hot water bath at 93°-95° C. and stretched 37% in the bath. The yarn was then collected in a pot in cake form, washed at 30° C. for 40 minutes at 52° C. in 0.50% aqueous sodium sulfide containing 0.05–0.10 sodium hydroxide, for 80 minutes at 30° C. in water, for 40 minutes at 30° C. in 0.01% acetic acid, for 40 minutes at 40° C. in 0.2% solution of an emulsified mineral oil controlled to a pH of 7 to 8, hydroextracted for 4.5 minutes, and dried at 70°-80° C. overnight.

Additional samples of fiber were prepared in the same manner, but using 80:20 and 50:50 (weight ratio) copolymers of acrylic acid and methacrylic acid. In the table below, the water retention values of the fibers are compared to the same fiber without added copolymer.

| Polymer Added | pH | % Solids | % Solids Calculated As Free Acid | Viscosity (Brookfield) Spindle No. 2 | Water Retention Valve (g/g)* |
|---|---|---|---|---|---|
| None | — | — | — | — | 0.97 |

| Polymer Added | pH | % Solids | % Solids Calculated As Free Acid | Viscosity (Brookfield) Spindle No. 2 | Water Retention Valve (g/g)* |
|---|---|---|---|---|---|
| 90/10 Acrylic Acid/Methacrylic Acid (AA/MAA) | 5.6 | — | 19.44 | 3750 | 1.36 |
| 80/20 Acrylic Acid/Methacrylic Acid | 5.4 | — | 25.08 | 1400 | 1.30 |
| 50/50 Acrylic Acid/Methacrylic Acid | 5.0 | — | 21.32 | 2150 | 1.27 |

*grams of water retained per gram of fiber

EXAMPLE 2

A solution of a homopolymer of acrylic acid (Rohm and Haas Acrysol A-1) was partially neutralized to a pH of 5.2 before injecting into a viscose solution at a concentration of 10% CIV, thoroughly mixed with the viscose and spun into a conventional acid spinbath containing about 5% sulfuric acid, about 20% sodium sulfate, about 1% zinc sulfate and 25 ppm lauryl pyridinium chloride at 56°–58° C. to coagulate and regenerate the cellulose to give a 22,488 denier fiber tow containing 7,496 filaments. The resulting tow was stretched 40% in air, run through a second bath at 92°–97° C. containing 3.2% sulfuric acid and about 6.15% total salts (NaSO₄ + ZnSO₄) and stretched 18% in the bath. The tow was then cut into 1 9/16 inches staple fiber lengths. The staple was then washed with water, then with 0.30% sodium sulfide solution, followed with water, than with a 0.175% sulfuric acid solution, followed with water, and then followed by a 0.20% sodium bicarbonate wash. A finish solution consisting of a 0.30% aqueous solution of sorbitan monoleate and ethoxylated stearic acid was applied before the fibers were dried for about ½ hour in a continuous oven set at about 80° C., for about ½ hour at about 70° C., and for about another ½ hour at about 50° C. The final moisture content was about 11%. Additional samples of fiber were prepared in the same manner, but using a homopolymer of polymethacrylic acid and a 50/50 by weight copolymer of acrylic acid and methacrylic acid. The various samples are given in the table below and results of the tests for Water Retention and Saline Retention (using a 1% by weight sodium chloride solution in place of water) are set forth.

| Polymer Added | pH | % Solids | % Solids Calculated As Free Acid | Viscosity (Brookfield) Spindle No. 2 | Water Retention Value (g/g) | Saline Retention Value (g/g) |
|---|---|---|---|---|---|---|
| Polyacrylic Acid | 5.2 | 27.8 | 20.9 | 488 | 1.26 | 1.11 |
| 50/50 Acrylic Acid/Methacrylic Acid | 5.2 | 26.3 | 20.9 | 1300 | 1.12 | 0.99 |
| Polymethacrylic Acid | 8.3 | 31.6 | 22.9 | 200 | 1.04 | 0.93 |

EXAMPLE 3

Fibers prepared in the same manner as Example 2 containing 5 and 10% CIV polyacrylic acid, 5 and 10% CIV of a 90/10 weight ratio of a copolymer of acrylic and methacrylic acid, and 5 and 10% of a 50/50 weight ratio of a copolymer of acrylic and methacrylic acid were evaluated in the Demand Wettability Test using the general procedure described in the test method and the external pressure and solutions described below.

| Additive | pH | % Solids | % Solids Calculated As Free Acid | Viscosity (Brookfield) Spindle No. 2 | 1% Sodium Chloride Solution | | | Synthetic Urine* 0.1 psi |
|---|---|---|---|---|---|---|---|---|
| | | | | | 0.1psi (ml/g)+ | 0.2psi (ml/g) | 0.3psi (ml/g) | |
| 5% CIV Polyacrylic Acid | 4.4 | 27.5 | 22.0 | 2550 | 18.3 | 16.4 | — | — |
| 5% CIV 90/10 AA/MAA | 5.0 | 27.4 | 21.2 | 3000 | 17.7 | 16.6 | — | — |
| 5% CIV 50/50 AA/MAA | 5.0 | 26.7 | 21.7 | 1837 | 18.9 | 17.5 | — | — |
| 10% CIV Polyacrylic Acid | 4.4 | 27.5 | 22.0 | 2550 | 16.3 | 14.6 | 14.9 | 16.6 |
| 10% CIV 90/10 AA/MAA | 5.3 | 27.4 | 21.0 | 2800 | 17.9 | 15.3 | 15.4 | 15.6 |
| 10% CIV 50/50 AA/MAA | 5.2 | 26.3 | 20.9 | 1300 | 17.6 | 15.8 | 15.7 | 17.5 |

+ml/g = ml. of fluid absorbed per gram of fiber
*Described by Weaver, Fanta, and Doane in "Highly Absorbent Starch Based Polymers" presented at International Nonwovens Disposable Association (INDA) 2nd Annual Symposium on Nonwoven Product Development, March 5 and 6, 1974, Washington, D. C., consisting of 97.09% distilled water, 1.94% urea, 0.8% NaCl, 0.11% MgSO₄ · 7H₂O₂, and 0.06% CaCl₂.

EXAMPLE 4

The three fibers of Example 3 containing 10% CIV of the three different polymers were carded, made into tampons and tested in the Syngina Device described by G. W. Rapp in his paper entitled "A comparison of The Absorptive Efficiency Of The Commercial Catamenial Tampons", published June, 1958, by the Department of Research, Loyola University, Chicago, Ill. The test fluid used was synthetic exudate described in U.S. Pat. No. 3,589,364 and consisting of 1% sodium chloride, 0.4% sodium carbonate, 10.0% glycerine, 0.46% carboxymethylcellulose and 88.14% distilled water.

The results of this test are described in the following table. The values are the average of five tests.

| Additive | Fluid Absorbed (g/g) |
|---|---|
| None | 4.70 |
| Polyacrylic Acid | 5.48 |
| 50/50 Acrylic/Methacrylic | 5.62 |

EXAMPLE 5

The fibers of Example 3 containing 10% CIV polyacrylic acid and 10% CIV of a 50/50 by weight copolymer of acrylic and methacrylic acid were carded into a fiber batt. Discs were made by compressing and heating three grams of these fibers in a one-inch diameter tube. These discs were then tested in the Demand Wettability Test using about 0.2 psi external weight and a 1% sodium chloride solution as the test fluid. The average values of 15 separate evaluations are shown in the following table.

| Polymer Added | Fluid Absorbed (g/g) |
| --- | --- |
| Polyacrylic Acid | 6.2 |
| 50/50 Acrylic/Methacrylic Acid | 6.4 |

EXAMPLE 6

Fibers were prepared in the same manner as Example 2 containing 15% and 20% CIV of a 50/50 weight ratio of a copolymer of acrylic acid and methacrylic acid. The retention values in water (WRV), saline (SRV), and synthetic exudate (ERVO (described in Example 4) are shown in the following table.

| Polymer Additive | pH | % Solids | % Solids Calculated As Free Acid | Viscosity (Brookfield) Spindle No. 2 | WRV (g/g) | SRV (g/g) | ERV (g/g) |
| --- | --- | --- | --- | --- | --- | --- | --- |
| None | | | | | 0.77 | 0.76 | 0.55 |
| 15% CIV 50/50 AA/MAA | 5.1 | 27.8 | 21.7 | 1475 | 1.28 | 1.10 | 1.04 |
| 20% CIV 50/50 AA/MAA | 5.1 | 27.8 | 21.7 | 1475 | 1.37 | 1.18 | 1.07 |

EXAMPLE 7

Fibers were prepared in the same manner as in Example 2 containing 15% CIV of 75:25, 50:50, 25:75, and 10:90 weight ratio of acrylic acid and methacrylic acid. The Water and Saline Retention Values are shown in the following table.

| Polymer Additive | pH | % Solids | % Solids Calculated As Free Acid | Viscosity (Brookfield) Spindle No. 2 | WRV | SRV |
| --- | --- | --- | --- | --- | --- | --- |
| 75/25 AA/MAA | 5.5 | 29.3 | 19.7 | 3075 | 1.41 | 1.20 |
| 50/50 AA/MAA | 13.0 | 26.9 | 15.9 | 2950 | 1.37 | 1.14 |
| 50/50 AA/MAA | 5.5 | 25.6 | 21.3 | 1775 | 1.33 | 1.12 |
| 25/75 AA/MAA | 5.8 | 25.6 | 20.0 | 3950 | 1.28 | 1.11 |
| 10/90 AA/MAA | 5.6 | 31.8 | 28.4 | 1000 | 1.11 | 1.01 |
| None | | | | | 0.77 | 0.76 |

EXAMPLE 8

Fibers prepared in the same manner as in Example 2 and containing 10, 15, and 20% CIV polyacrylic acid and 10, 15, and 20% CIV of a 50/50 weight ratio of copolymer of acrylic and methacrylic acid were carded on a conventional 40-inch flat top card at a speed of 16 pounds per hour to give a sliver weight of 65 grains per yard.

The sliver cohesion values are given in the following table:

| | Sliver Cohesion (g/gr.)* | |
| --- | --- | --- |
| Amount of Polymer Added (CIV) | Polyacrylic Acid | 50/50 Acrylic/ Methacrylid acid |
| 10% | 5.3 | 7.9 |
| 15% | 4.8 | 7.4 |
| 20% | 5.5 | 13.8 |
| None | 7.9 | |

*Grams per grain of fibers.

All Viscosites given in the above examples are measured with a Brookfield Viscometer with a Spindle No. 2.

It is clear from the results in Example 1 that the copolymers containing various ratios of acrylic acid to methacrylic acid have significantly increased water retention values over regular rayon. Another interesting feature of this example is the apparent decrease in water retention value as the amount of methacrylic acid in the copolymer is increased. This superiority in water retention value for polyacrylic acid over polymethacrylic acid is demonstrated clearly in Example 2. This difference is not unexpected if one considers that the water retention value is related to the swelling of the fiber and that the swelling of an anionic polyelectrolyte network, such as polyacrylic acid or a copolymer of polyacrylic acid and polymethacrylic acid, is proportional to the degree of ionization of the polyelectrolyte. If one considers that the degree of ionization of polyacrylic acid is greater than the degree of ionization of polymethacrylic acid, the results in Examples 1 and 2 are not unexpected. However, the water retention value is not the only factor that determines the performance of an absorbent material. There are many test methods in the literature that attempt to measure the performance of fibers under simulated end use conditions. Evaluation of fibers containing the copolymers of the invention by the Demand Wettability and Syngina methods in Examples 3, 4, and 5 show that the copolymers of acrylic acid and methacrylic acid actually exhibit greater absorbency values than polyacrylic acid. A ready explanation of this rather unexpected result is not available at this time. It is apparent, however, that a mechanism other than the ionization of the carboxylic acid group is now affecting the absorbency properties of the fiber in certain end use performance areas.

What is claimed is:

1. A highly absorbent cellulosic fiber containing in a physical admixture with cellulose from 2% to about 40% of an alkali metal salt or ammonium salt of a copolymer of acrylic acid and methacrylic acid based on the weight of cellulose, the ratio of acrylic acid to methacrylic acid in the copolymer being from 90:10 to 10:90 by weight.

2. The article of claim 1 in the form of a tampon.

3. The fiber of claim 1 wherein the cellulose is regenerated from a viscose solution.

4. The fiber of claim 1 wherein the ratio of acrylic acid to methacrylic acid is 50:50 by weight.

5. A staple cellulose fiber having improved absorbency for body fluids and improved carding characteristics and adapted to be used in making non-woven absorbent articles which are to be associated with the body for the absorption of body fluids, said fiber containing in admixture with cellulose from 2 to about 40% of an alkali metal or ammonium salt of a copolymer of acrylic acid and methacrylic acid, based on the weight of the cellulose, the ratio of acrylic acid to methacrylic acid in the copolymer being from 90:10 to 10:90 by weight.

6. The fiber of claim 5 wherein the cellulose is regenerated from a viscose solution.

7. An article of manufacture comprising highly absorbent fibers having a matrix of regenerated cellulose and from 2 to about 40% of an alkali metal or ammonium salt of a copolymer of acrylic acid and methacrylic acid in physical mixture with the cellulose, the ratio of acrylic acid to methacrylic acid units in the copolymer being from 90:10 to 10:90 by weight.

8. The article of claim 7 wherein the said ratio is 50:50 by weight.

9. A method for improving the absorbency and fluid retention of a regenerated cellulose fiber for body fluids which comprises mixing with a viscose solution from 2 to about 40%, based on the weight of cellulose in the solution, of an alkali metal salt or ammonium salt of a copolymer of acrylic acid or methacrylic acid and spinning the mixture under conditions which avoid chemical reaction of the copolymer with the cellulose to form a fiber having an absorbency for body fluids which is greater than that of a fiber made from the same viscose solution without the copolymer.

* * * * *